US00PP16926P2

(12) United States Plant Patent
Dümmen

(10) Patent No.: US PP16,926 P2
(45) Date of Patent: Aug. 1, 2006

(54) ***GERANIUM* PLANT NAMED 'DUEPALAV'**

(50) Latin Name: *Pelargonium peltatum*
Varietal Denomination: Duepalav

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 11/171,796

(22) Filed: Jun. 30, 2005

(51) Int. Cl.
*A01H 5/00* (2006.01)

(52) U.S. Cl. ..... Plt./332

(58) Field of Classification Search ..... Plt./332
See application file for complete search history.

(56) References Cited

PUBLICATIONS

GTITM UPOVROM Citation for 'Duepalav' as per QZ PBR 20031121; Jun. 19, 2003.*

* cited by examiner

*Primary Examiner*—Kent Bell
(74) *Attorney, Agent, or Firm*—C. A. Whealy

(57) ABSTRACT

A new and distinct cultivar of Ivy *Geranium* plant named 'Duepalav', characterized by its upright and outwardly spreading plant habit; freely basal branching habit; freely flowering habit; and lavender-colored double flowers.

1 Drawing Sheet

Botanical denomination: *Pelargonium peltatum.*
Cultivar designation: 'Duepalav'.

BACKGROUND OF THE INVENTION

The present invention relates to a new and distinct cultivar of Ivy *Geranium* plant, botanically known as *Pelargonium peltatum,* and hereinafter referred to by the name 'Duepalav'.

The new Ivy *Geranium* is a product of a planned breeding program conducted by the Inventor in Rheinberg, Germany. The objective of the breeding program was to develop new compact and freely-flowering Ivy *Geraniums* with attractive flower and foliage colors.

The new Ivy *Geranium* originated from a cross-pollination made by the Inventor on May 1, 1999, of a proprietary selection of *Pelargonium peltatum* identified as code number F-01-13, not patented, as the female, or seed, parent with a proprietary selection of *Pelargonium peltatum* identified as code number F-19-03, not patented, as the male, or pollen, parent. The cultivar Duepalav was discovered and selected by the Inventor as a flowering plant within the progeny from this cross in a controlled environment in Rheinberg, Germany in May, 2002.

Asexual reproduction of the new cultivar by terminal vegetative cuttings at Rheinberg, Germany since May, 2002 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Duepalav'. These characteristics in combination distinguish 'Duepalav' as a new cultivar and distinguish it from other known Ivy *Geranium* cultivars:

1. Upright and outwardly spreading plant habit.
2. Freely basal branching habit.

3. Freely flowering habit.
4. Lavender-colored double flowers.

Compared to plants of the female parent selection, plants of the new Ivy *Geranium* are stronger. Plants of the new Ivy *Geranium* and the male parent selection differ in petal coloration.

The new Ivy *Geranium* can be compared to plants of the cultivar Lilac, not patented. In side-by-side comparisons conducted in Rheinberg, Germany, plants of the new Ivy *Geranium* differed from plants of the cultivar Lilac in the following characteristics:

1. Plants of the new Ivy *Geranium* were more compact than plants of the cultivar Lilac.
2. Leaves of the new Ivy *Geranium* had shorter internodes than plants of the cultivar Lilac.
3. Plants of the new Ivy *Geranium* were more freely branching than plants of the cultivar Lilac.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy *Geranium*. The photograph comprises a side perspective view of a typical flowering plant of 'Duepalav' grown in a container.

DETAILED BOTANICAL DESCRIPTION

The cultivar Duepalav has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5 cm containers. Plants were pinched about three weeks after planting. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification: *Pelargonium peltatum* cultivar Duepalav.

Parentage:

*Female parent.*—Proprietary selection of *Pelargonium peltatum* identified as code number F-01-13, not patented.

*Male parent.*—Proprietary selection of *Pelargonium peltatum* identified as code number F-19-03, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine; fibrous; white in color.

*Rooting habit.*—Freely branching.

Plant description:

*General appearance.*—Upright and outwardly spreading plant habit, rounded plant form; densely foliated.

*Growth and branching habit.*—Moderately vigorous. Freely basal branching, about four to five lateral branches per plant.

*Plant height.*—About 20 cm.

*Plant width.*—About 21 cm.

*Lateral branches.*—Length: About 25 cm. Internode length: About 3.3 cm. Texture: Smooth. Color: 144A.

*Foliage description.*—Arrangement: Alternate, single. Length: About 5.9 cm. Width: About 6.6 cm. Shape: Reniform. Apex: Acute. Base: Peltate. Margin: Crenate. Venation pattern: Palmate. Texture, upper and lower surfaces: Smooth, glabrous. Color: Developing and fully expanded foliage, upper surface: 137A; zonation pattern, 147A in color and about 5 mm in width. Developing and fully expanded foliage, lower surface: 137C. Venation, upper surface: 144A. Venation, lower surface: 144B. Petiole: Length: About 4.1 cm. Diameter: About 2 mm. Color, upper and lower surfaces: 144A.

Flower description:

*Flower arrangement.*—Lavender-colored double flowers arranged in rounded hemispherical umbels arising from apical leaf axils. Umbels displayed above the foliage on upright peduncles. Flowers rounded in form. Umbels persistent, flowers not persistent. Flowers not fragrant.

*Quantity of flowers.*—Freely flowering; plants have about seven open umbels with about eight to nine flowers per umbel.

*Flowering season.*—Flowering continuous spring through summer.

*Flower longevity.*—Flowers last about five to seven days on the plant.

*Umbel size.*—Diameter: About 7.5 cm. Height: About 4.3 cm.

*Flower size.*—Diameter: About 4.5 cm. Depth (height): About 1.8 cm.

*Flower buds.*—Length: About 1.1 cm. Diameter: About 6.5 mm. Shape: Ovoid. Color: 144A.

*Petals.*—Quantity per flower: About five. Length: About 2.8 cm. Width: About 1.5 cm. Shape: Obovate. Apex: Rounded. Base: Attenuate. Margin: Sinuate. Texture, upper and lower surfaces: Smooth. Color: When opening and fully opened, upper surface: 76A; towards the base, 64B; color becoming closer to 76B with development. When opening and fully opened, lower surface: 76B.

*Petaloids.*—Quantity per flower: About 13. Length: About 2.8 cm. Width: About 1.7 cm. Shape: Obovate. Apex: Rounded. Base: Attenuate. Margin: Sinuate. Texture, upper and lower surfaces: Smooth. Color: When opening and fully opened, upper surface: 76A. When opening and fully opened, lower surface: 76B.

*Sepals.*—Quantity per flower: About eight to nine, arranged in a single whorl. Length: About 1.2 cm. Width: About 3 mm. Shape: Elongated, tapering. Apex: Apiculate. Margin: Entire. Texture, upper and lower surfaces: Smooth, glabrous. Color, upper and lower surfaces: 144A; towards the margins, 144B.

*Peduncle* (*umbel stem*).—Length: About 10.3 cm. Diameter: About 1 cm. Angle: Erect. Strength: Moderately strong. Texture: Smooth, glabrous. Color: 144A.

*Pedicel* (*individual flower stem*).—Length: About 1.9 cm. Diameter: About 2 mm. Angle: Erect. Strength: Moderately strong. Texture: Pubescent. Color: 144A.

*Reproductive organs.*—Androecium: Anther quantity per flower: About four or five. Anther length: About 3 mm. Anther shape: Ovate. Anther color: 61B. Pollen amount: Moderate. Pollen color: 28A. Gynoecium: Pistil quantity per flower: One. Pistil length: About 1.3 cm. Stigma shape: Crested. Stigma color: 71A. Style length: About 4 mm. Style color: 2D. Ovary color: Close to 144A.

*Seed/fruit.*—Development of seeds and fruit have not been observed.

Disease/pest resistance: Plants of the new Ivy *Geranium* have not been observed to be resistant to pathogens and pests common to Ivy *Geraniums*.

Temperature tolerance: Plants of the new Ivy *Geranium* have been observed to be tolerant to temperatures ranging from 5° to 40° C.

It is claimed:

1. A new and distinct cultivar of Ivy *Geranium* plant named 'Duepalav', as herein illustrated and described.

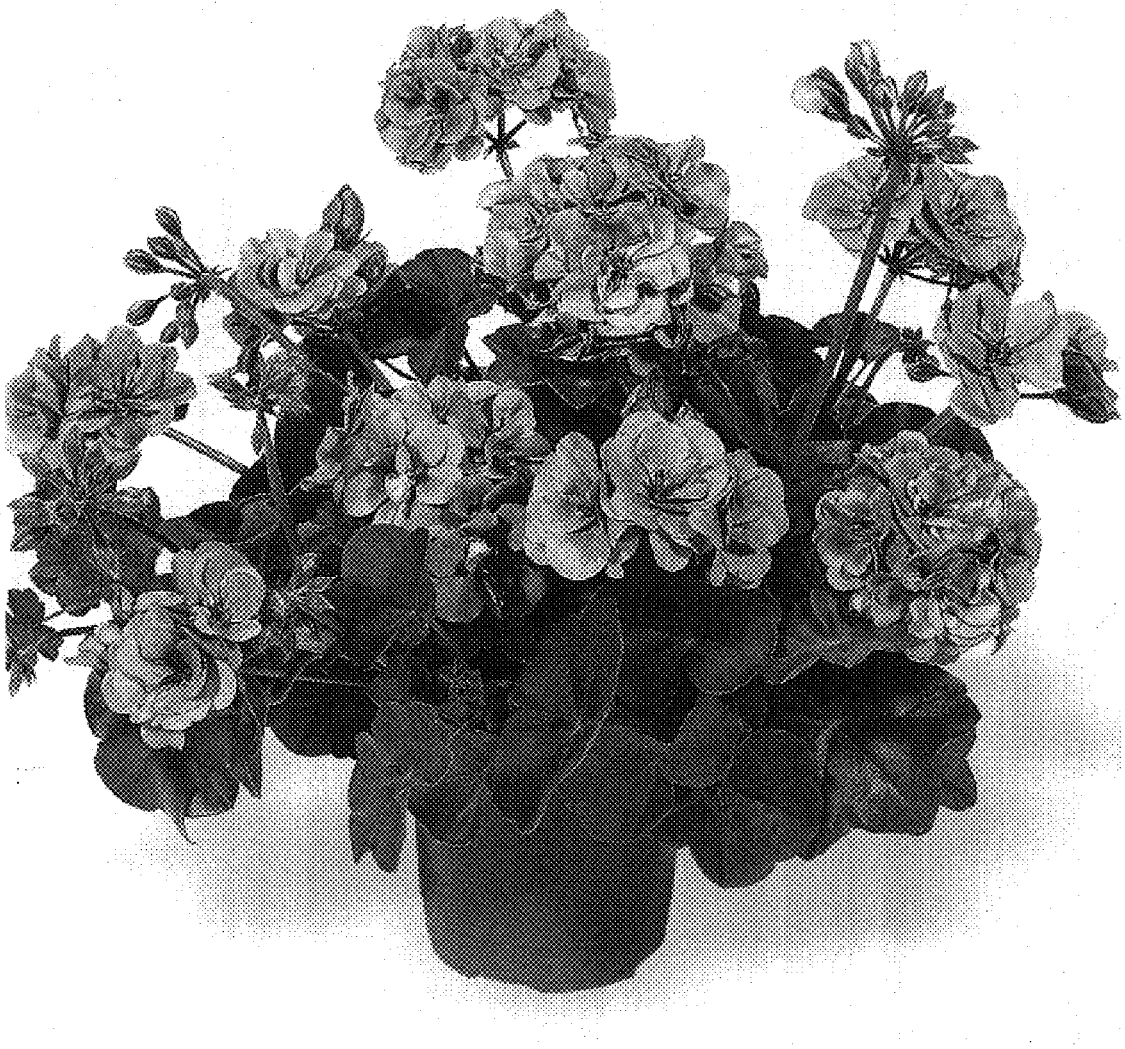

* * * * *